United States Patent [19]

Kohsaka et al.

[11] Patent Number: 4,827,020

[45] Date of Patent: May 2, 1989

[54] PROPARGYL AMIDE PRECURSOR TO 1-PROPARGYL-2,4-DIOXOIMIDAZOLIDINE

[75] Inventors: Hideo Kohsaka, Takarazuka; Yoshihiko Oue, Ibaraki, both of Japan

[73] Assignee: Sumitomo Chemical Company, Limited, Osaka, Japan

[21] Appl. No.: 164,321

[22] Filed: Mar. 4, 1988

[30] Foreign Application Priority Data

Mar. 24, 1987 [JP] Japan .................................. 62-70943
Mar. 26, 1987 [JP] Japan .................................. 62-73356

[51] Int. Cl.$^4$ .......................................... C07C 125/065
[52] U.S. Cl. .................................. 560/159; 548/308; 560/157
[58] Field of Search ......................... 548/308; 560/159

[56] References Cited

U.S. PATENT DOCUMENTS 3,769,271 10/1973 Southard ......................... 560/159 X
4,133,964 1/1979 Metcalf et al. .................. 560/159 X
4,176,189 11/1979 Itaya et al. ...................... 548/309 X

FOREIGN PATENT DOCUMENTS 0077721 4/1983 European Pat. Off. .

OTHER PUBLICATIONS

Ware, E., Chem. Rev., 46, 403-70 (1950).
Koenigs, E. et al., Chem. Ber., 41, 4427-43 (1908).
Clarke, C., et al., J. Chem. Soc., 99, 319-25 (1911).
Chem. Abstracts 17, 1802 (1923) [Ger. No. 335,993].
Chem. Abstracts, 30, 3592 (1936) [Swiss No. 177,411, 9/2/35].
Effenberger, F., et al., Chem. Ber., 114, 173-89 (1981).
Chem. Abstracts, 30, 8530 (1936) [Swiss No. 181,175, 181,176, 2/17/36].

Primary Examiner—Richard A. Schwartz
Attorney, Agent, or Firm—Stevens, Davis, Miller & Mosher

[57] ABSTRACT

1-propargyl-2,4-dioxoimidazolidine is a very useful intermediate for synthesizing insecticidal and acaricidal compounds of pyrethroid type. Here are disclosed a method for producing 1-propargyl-2,4-dioxoimidazolidine, the starting material compounds thereof and a method for producing said starting material compounds. According to the present invention, said useful intermediate can be easily produced than before.

1 Claim, No Drawings

PROPARGYL AMIDE PRECURSOR TO 1-PROPARGYL-2,4-DIOXOIMIDAZOLIDINE

The present invention relates to a method for producing 1-propargyl-2,4-dioxoimidazolidine having the following formula (I) (hereinafter referred to as Compound I):

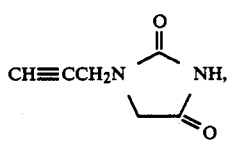
(I)

starting material compounds thereof and a method for producing said starting material compounds.

More particularly, it relates to a method for producing Compound I, which is a useful intermediate for synthesizing pyrethroid compounds having the following general formula (II) (hereinafter referred to as Compound II):

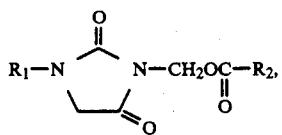
(II)

wherein $R_1$ represents a lower alkyl group, a lower alkenyl group or a lower alkynyl group; $R_2$ represents the group having any of the following formulae:

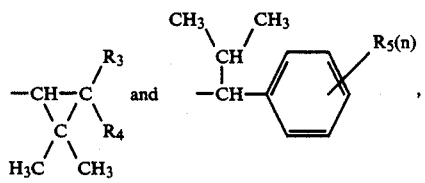

wherein $R_3$ represents hydrogen or methyl group; $R_4$ represents methoxyiminomethyl group, 2,2-dimethylvinyl group or 2,2-dihalovinyl group; $R_5$ represents methyl group, methoxy group, a halogen or 3,4-methylenedioxy group; and n represents 1 or 2.

It is known that the compound having the general formula (II) mentioned above, which has an excellent insecticidal and acaricidal activity, can be produced by reacting an alcohol compound having the general formula (IV) (hereinafter referred to as Compound )V):

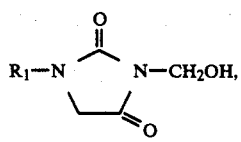
(IV)

wherein $R_1$ represents the same meaning as above, derived from a 1-substituted-2,4-dioxoimidazolidine having the following general formula (III) (hereinafter referred to as Compound III):

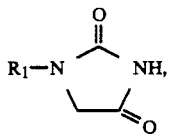
(III)

wherein $R_1$ represents the same meaning as above, with a carboxylic acid having the following general formula (V) (hereinafter referred to as Compound V):

$$R_2—COOH \qquad (V),$$

wherein $R_2$ represents the same meaning as above, or a reactive derivative thereof (see U.S. Pat. No. 4,176,189).

Also, there has been know a method for producing said 1-substituted-2,4-dioxoimidazolidine having the general formula (III) mentioned above comprising reacting N-substituted-α-amino acid with potassium cyanate or urea [Chemical Review", Vol. 46, pages 407 and 413 (1950)].

However, the above-mentioned method for producing 1-substituted-2,4-dioxoimidazolidine has such an inconvenience that in the case where the N-propargyl substituted compound is intended, industrially unavailable N-propargyl glycine must be used.

In recognition of this situation, the present inventors have made extensive studies about the method for producing Compound I, which is an intermediate for insecticides or acaricides, to find that Compound I can be obtained easily and in high yield by reacting an alkyl ester of N-propargyl-N-alkoxycarbonylglycine having the following general formula (VI) (hereinafter referred to as Compound VI):

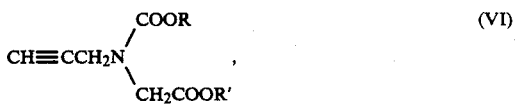
(VI)

wherein R and R' represent the same or different lower alkyl groups having one to four carbon atoms, with aqueous or gaseous ammonia to obtain an amide compound having the following general formula (VII) (hereinafter referred to as Compound VII):

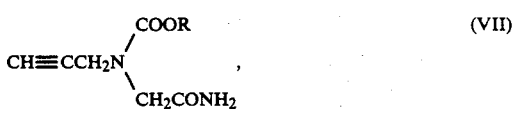
(VII)

wherein R represents the same meaning as above, followed by further reacting said amide compound with a base.

The amidation reaction for producing the amide compound of the general formula (VII) from the ester of the general formula (VI) can be carried out by reacting said ester with excess aqueous ammonia or by bubbling of gaseous ammonia into a solution of said ester in a solvent at 0°–100° C. at atmospheric pressure. Specific examples of the usable slvents are water; alcohols such as methanol, ethanol and the like; ethers such as dioxane, tetrahydrofuran and the like; mixtures thereof and the like. This amidation reaction can be accelerated by adding thereto an alkoxide such as sodium methoxide, sodium ethoxide and the like. Moreover, when an alkoxide is added to the solution of the ester and the solution is heated, Compound I can be also obtained.

The thus obtained amide compound of the general formula (VII) can be used in the succeeding process without isolating and purifying the same.

The amidation is followed by a process for producing Compound I by reacting the amide compound of the general formula (VII) with a base.

In this reaction, the base is usually used in an amount of at least one equivalent per equivalent of the amide compound of the general formula (VII). Specific examples of the usable bases are hydroxides such as sodium hydroxide, potassium hydroxide, lithium hydroxide, barium hydroxide and the like; alkoxides such as sodium methoxide, sodium ethoxide, potassium t-butoxide and the like; ammonia and the like. When ammonia is used as the base, said reaction is usually carried out under the pressure of 3-100 kg/cm$^2$.

The reaction temperature is usually 10°-200° C., and the reaction time is usually from 15 minutes to 5 hours.

Said reaction is usually carried out in an inert solvent. Specific examples of the inert solvent are water; alcohols such as methanol, ethanol and the like; ethers such as dioxane, tetrahydrofuran and the like; mixtures thereof and the like.

After the completion of the reaction, the resulting solution is subjected to a neutralization by an acid such as hydrogen chloride gas, hydrochloric acid, sulfuric acid and the like. Then the solvent is distilled off and inorganic salt is filtered off from the extract by a solvent such as alcohols (methanol, ethanol and the like), acetonitrile, acetone or the like. Thereafter the filtrate is concentrated. If necessary, there may be utilized one or more treatment such as recrystallization, purification by means of a chromatograph or the like.

A more efficient production of Compound I can be realized by successively carrying out the above-mentioned two processes in the same vessel. Such a reaction can be carried out by reacting the compound having the general formula (VI) with ammonia under a pressure or in the presence of a base.

Specific examples of the usable solvents are water; alcohols such as methanol, ethanol and the like; ethers such as dioxane, tetrahydrofuran and the like; mixtures thereof and the like.

When the reaction under a pressure is intended, it is usually carried out under 3-100 kg/cm$^2$ at 10°-200° C. Whereas the reaction in the presence of a base is intended, it is usually carried out at 50°-200° C., preferably 50°-110° C. Specific examples of the usable bases are hydroxides such as sodium hydroxide, potassium hydroxide, lithium hydroxide, barium hydroxide and the like; alkoxides such as sodium methoxide, sodium ethoxide, potassium t-butoxide and the like.

The starting material compound used in the present invention can be obtained by reacting the compound having the following general formula (VIII) (hereinafter referred to as Compound (VIII):

(VIII)

wherein R and R' represent the same meanings as above, with a propargyl halide in the presence of a base. The compound of the general formula (VIII) can be obtained by the process disclosed in "Chemische Berichte", Vol. 114, pages 173-189 (1981).

In this reaction, the propargyl halide and the base are used in an amount of 1-10 equivalents and 1-1.5 equivalents per equivalent of the compound of the general formula (VIII), respectively.

The said reaction is usually carried out in a solvent, specific examples of which are alcohols such as methanol, ethanol, t-butanol and the like; ethers such as tetrahydrofuran, 1,2-dimethoxyethane and the like; aromatic hydrocarbons such as benzene, toluene and the like; dimethyl sulfoxide; N,N-dimethyl formamide (DMF); mixtures thereof and the like. Specific examples of the usable base are sodium hydride, potassium t-butoxide and the like. The reaction temperature is usually $-30°$-120° C., preferably 0°-50° C.; and the reaction time is usually from 15 minutes to 10 hours. This reaction is preferred to be carried out in nitrogen atmosphere.

The following examples serve to give specific illustrations of the practice of the present invention but they are not intended in any way to limit the scope of the present invention.

EXAMPLE 1

Preparation of Compound I from Compound VI 650 mg of methyl N-propargyl-N-methoxycarbonylglycinate were dissolved in 20 ml of methanol. Then 700 mg of 28% methanol solution of sodium methoxide were added thereto. Gaseous ammonia were bubbled into the mixture at room temperature. After the stirring at room temperature for 2 hours, the reaction mixture was refluxed on heating for 30 minutes. Then the resulting mixture was cooled down to room temperature and was subjected to a neutralization with hydrogen chloride gas. Thereafter the neutralized mixture was subjected to concentration and removing of inorganic salt by filtration. From the filtrate, the solvent was evaporated off to quantitatively obtain 510 mg of crude 1-propargyl-2,4-dioxoimidazolidine.

EXAMPLE 2

Preparation of Compound I from Compound VI 3.0 g of methyl N-propargyl-N-methoxycarbonylglycinate were dissolved in 40 ml of 28% aqueous ammonia. Then the mixture was maintained under the pressure of 10-13 kg/cm$^2$ at 100°-110° C. for an hour. Then the solvent was evaporated off from the reaction mixture. The resulting mixture was subjected to a column chromatography on silica gel (5:1 ethyl acetate:methanol as eluent) to obtain 0.65 g of 1-propargyl-2,4-dioxoimidazolidine.

EXAMPLE 3

Preparation of Compound VII from Compound VI 3.9 g of methyl N-propargyl-N-methoxycarbonylglycinate were added to the mixture of 100 ml of 28% aqueous ammonia and 10 ml of methanol and stirred for 10 hours at room temperature. Then the solvent was evaporated off from the reaction mixture. The residue was chromatograhed on silica gel to obtain 3.0 g of N-propargyl-N-methoxycarbonylglycinamide (melting point: 77°-80° C.).

EXAMPLE 4

Preparation of Compound I from Compound VII 2.0 g of N-propargyl-N-methoxycarbonylglycinamide were added to the mixture of 5 ml of methanol and 2.5 ml of 20% aqueous solution of sodium hydroxide and maintained at 70° C. for an hour. After cooled down to room temperature; the reaction mixture was neutralized with concentrated hydrochloric acid followed by concentrating and drying the same by an evaporation under reduced pressure. Then it was extracted with acetonitrile and sodium chloride was removed off from the extract by filtration. The solvent was evaporated off from the filtrate to obtain 1.4 g of 1-propargyl-2,4-dioxoimidazolidine (melting point: 124°–125° C.).

EXAMPLE 5

Preparation of Compound I from Compound VII 1.5 g of N-methoxycarbonylglycinamide were added to 30 ml of methanol solution containing 0.5 g of sodium methoxide and maintained at 70° C. for an hour. After cooled down to room temperature, the reaction mixture was neutralized with concentrated hydrochloric acid. Then the solvent was evaporated off from the mixture. The residue was subjected to an extraction with acetonitrile and inorganic salt was removed by filtration. Thereafter the solvent was evaporated off from the filtrate to obtain 0.96 g of 1-propargyl-2,4-dioxoimidazolidine.

EXAMPLE 6

Preparation of Compound VI 5.0 g of methyl N-methoxycarbonylglycine were dissolved in 30 ml of N,N-dimethylformamide. Then ice-cooling the mixture, 1.5 g of sodium hydride (60% oil dispersion) were added thereto under a nitrogen atmosphere and stirred for 20 minutes. Thereafter 6.0 g of propargyl bromide were dropped thereto over 15 minutes and further stirred for 40 minutes. Then the reaction mixture was poured into ice-water and sodium chloride was added thereto to saturate the same. Then the aqueous layer was washed with hexane and it was subjected to two times of extraction with 100 ml of ether. The ether layers were combined together and dried over anhydrous magnesium sulfate and the solvent was evaporated off to obtain 3.9 g of methyl N-propargyl-N-methoxycarbonylglycinate ($n_D^{18}$: 1.4891).

EXAMPLE 7

Preparation of Compound VI 3.0 g of methyl N-methoxycarbonylglycinate were dissolved in 30 ml of N,N-dimethylformamide. Ice-cooling the mixture, 820 g of sodium hydride (60% oil dispersion) were added thereto under a nitrogen atmosphere and stirred for 20 minutes. Then 2.3 g of propargyl chloride were dropped thereto over 10 minutes and further stirred for 40 minutes. The reaction mixture was poured into ice-water and then sodium chloride was added thereto to saturate the same. Thereafter the aqueous layer was washed with hexane and it was subjected to two times of extraction with 100 ml of ether. The ether layers were combined together and dried over anhydrous magnesium sulfate and the solvent was evaporated off to obtain 1.95 g of methyl N-propargyl-N-methoxycarbonylglycinate.

EXAMPLE 8

Preparation of Compound VI 100 g of ethyl N-methoxycarbonylglycinate were dissolved in 600 ml of N,N-dimethylformamide. Then ice-cooling the mixture, 25 g of sodium hydride (60% oil dispersion) were added thereto under a nitrogen atmosphere. After the reaction mixture was stirred for 2 hours, 81.3 g of propargyl bromide were dropped thereto over 2 hours. After the mixture was further stirred for an hour, the reaction product was poured into water and the aqueous layer was washed with hexane. Then it was subjected to three times of extraction with 100 ml of ether. The ether layers were combined together and dried over anhydrous magnesium sulfate and the solvent was evaporated off to obtain 79.8 g of ethyl N-propargyl-N-methoxycarbonylglycinate.

What is claimed is:

1. An amide compound having the following formula:

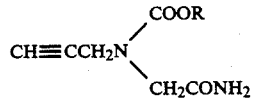

wherein R represents a lower alkyl group.

* * * * *